United States Patent [19]
Ventura et al.

[11] Patent Number: 5,731,104
[45] Date of Patent: Mar. 24, 1998

[54] BATTERIES, CONDUCTIVE COMPOSITIONS, AND CONDUCTIVE FILMS CONTAINING ORGANIC LIQUID ELECTROLYTES AND PLASTICIZERS

[75] Inventors: Susanna C. Ventura, Los Altos; Subhash C. Narang, Redwood City; Georgina Hum; Peikang Liu, both of Menlo Park; Prema Ranganathan, Cupertino, all of Calif.; Luying Sun, Stoughton, Mass.

[73] Assignee: SRI International, Menlo Park, Calif.

[21] Appl. No.: 807,215

[22] Filed: Feb. 28, 1997

Related U.S. Application Data

[63] Continuation of Ser. No. 372,193, Jan. 13, 1995, abandoned.

[51] Int. Cl.$^6$ .................................................. H01M 6/04
[52] U.S. Cl. ............................................. 429/188; 252/62.2
[58] Field of Search ................................. 204/418, 420, 204/296; 359/269, 270; 456/450; 528/10, 30; 568/595, 603; 429/188, 192; 252/622

[56] References Cited

U.S. PATENT DOCUMENTS

| | | | |
|---|---|---|---|
| 2,379,249 | 6/1945 | Muskat | 252/73 |
| 2,844,451 | 7/1958 | Alpert et al. | 44/70 |
| 3,072,613 | 1/1963 | Whelan et al. | 260/77.5 |
| 4,273,726 | 6/1981 | Altuglu | 260/463 |
| 4,423,235 | 12/1983 | Burgard et al. | 549/229 |
| 4,840,858 | 6/1989 | Furukawa et al. | 429/197 |
| 5,061,581 | 10/1991 | Narang et al. | 429/192 |
| 5,085,952 | 2/1992 | North | 429/192 |
| 5,102,751 | 4/1992 | Narang et al. | 429/192 |
| 5,130,211 | 7/1992 | Wilkinson et al. | 429/198 |
| 5,219,683 | 6/1993 | Webber | 429/197 |
| 5,300,375 | 4/1994 | Chaloner-Gill | 429/192 |
| 5,340,889 | 8/1994 | Crawford et al. | 525/523 |
| 5,358,620 | 10/1994 | Golovin et al. | 204/421 |
| 5,370,809 | 12/1994 | Ishida et al. | 252/52 A |

FOREIGN PATENT DOCUMENTS

WO 95 29512  11/1995  WIPO .

OTHER PUBLICATIONS

Database Crossfire, Beilstein Informations Systeme GmbH, Frankfurt DE XP002004938, XP002004939, XP002004940, XP002004941, XP002004942, XP002004943, XP00200494, XP002004945, XP002004946, XP002004947, XP002004948, XP002004949, XP002004950, XP002004951 No dates available.

Narang et al., "Solid polymer electrolytes for rechargeable batteries. Final report," Report No. LBL-32059 (Department of Energy; Feb. 1992). Abstract only.

Narang et al., "Solid polymer electrolytes for rechargeable batteries. Final report," Report No. LBL-29829 (Department of Energy; Nov. 1990). Abstract only.

Arakawa et al., "The Cathodic Decomposition of Propylene Carbonate in Lithium Batteries" *J. Electroanal. Chem.* 219:273–280 (1987) No month available.

Shu et al., "Electrochemical Intercalation of Lithium into Grahite" *J. Electrochem. Soc.* 140:922–927 (1993) No month available.

Shu et al., "Effect of 12 Crown 4 on the electrochemical Intercalation of Lithium into Grahite" *J. Electrochem. Soc.* 140:L101–L103 (1993) No month available.

Feast et al., The Synthesis and Characteristics of Some Flourinated Aliphatic, Aliphatic and Aliphatic Ether Polycarbonates, Br. Polym. J., 16(4), 314–20, 1984, abstract only.

*Primary Examiner*—Kathryn L. Gorgos
*Attorney, Agent, or Firm*—Reed & Robins LLP

[57] ABSTRACT

Novel batteries formulated with compositions comprising liquid electrolyte plasticizers having enhanced ambient temperature conductivity are provided. These plasticizers have the following general structures

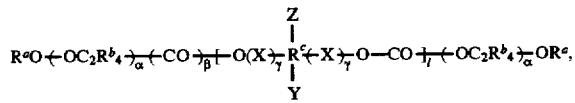

in which $R^a$, $R^b$, $R^c$, X, Y, Z, $\alpha$, $\beta$, $\gamma$, and 1 are as defined herein. Novel compositions and films comprising these plasticizers are also provided.

24 Claims, 1 Drawing Sheet

BATTERIES, CONDUCTIVE COMPOSITIONS, AND CONDUCTIVE FILMS CONTAINING ORGANIC LIQUID ELECTROLYTES AND PLASTICIZERS

This application is a continuation of application Ser. No. 08/372,193 filed on Jan. 13, 1995 now abandoned.

REFERENCE TO GOVERNMENT GRANT

This invention was made with Government support. The Government has certain rights in the invention.

TECHNICAL FIELD

The present invention relates generally to novel liquid electrolyte plasticizers. The invention additionally relates to conductive compositions containing these novel plasticizers in combination with one or more solid polymer electrolytes. Also within the scope of the present invention, there are plasticizer-containing conductive films, and methods of manufacturing such films. The invention further relates to the use of these liquid electrolyte plasticizers, conductive compositions and conductive films in solid-state batteries, fuel cells, sensors, supercapacitors, electrochromic devices and the like.

BACKGROUND OF THE INVENTION

A number of solvent-free polymer electrolytes are known, and there has been considerable interest in the potential use of such electrolytes in electrochemical devices such as solid-state batteries, fuel cells, sensors, supercapacitors and electrochromic devices. Polymer electrolytes in general have a number of desirable features, i.e., they are inherently safe in operation, they avoid the leakage and drying problems experienced with liquid compositions, and they are further relatively processable. An additional advantage of solid polymer electrolytes is their ability to deform and thus maintain interfacial contact with electrodes. Finally, polymer electrolytes may be cast in thin films to minimize resistance of the electrolyte and to reduce volume and weight.

Among the polymers which have been tested for use in solvent-free electrolyte systems, there are those based upon the linear-chain polyethers, poly(ethylene oxide) ("PEO") and poly(propylene oxide) ("PPO"), with associated alkali metal salts such as lithium salts. Representative PEO and PPO polymers are described by Le Nest et al., in *Polymer Communications* 28:302-305 (1987) and by Tsuchida et al., *Macromolecules* 88:96-100 (1988). However, such electrolytes display conductivity in the range of practical use (e.g., $\sigma=10^{-5}-10^{-3}$ S/cm) only at temperatures well above room temperature. Further, the reported linear-chain polyether electrolytes exhibit an ion transport number that is significantly lower than one, as both the anion and cation have ionic mobility and eventually account for the polymer electrolyte conductivity. Accordingly, a considerable amount of research has been focused on providing conductive solid polymer electrolytes capable of exhibiting conductivities in the range of their liquid electrolyte counterparts.

Attempts at improving the ionic conductivity of such polymer electrolytes have included the synthesis of new polymeric materials such as cation conductive phosphazene and siloxane polymers which exhibit better conductivity at room temperature than the linear-chain polyether electrolytes. In this regard, one class of polymers of interest are the polyphosphazene sulfonates as reported by Ganapathiappan et al. in both *Macromolecules* 21:2299-2301 (1988) and the *Journal of the American Chem. Soc.* 111:4091-4095 (1989); see also Chen et al., *Chem. of Materials* 1:483-484 (1984).

Other attempts at improving ionic conductivity have dealt with comb-like polymers with oligo-oxyethylene side chains anchored to a polyphospazene, polymethacrylate or polysiloxane backbone. See, e.g., Blonsky et al., *J. Am. Chem. Soc.* 106:6854-6855 (1984), Bannister et al., *Polymer* 25:1600-1602 (1984) and Spindler et al., *J. Am. Chem. Soc.* 110:3036-3043 (1988). Since the movement of ions through the polymer matrix proceeds essentially by a free volume mechanism, polymers with flexible side chains are generally preferred. Cation transport polymer electrolytes based on cation conductive siloxane comb polymers are reported by Zhou et al., *Poly. Comm.* 30:52-55 (1989) and by Rietman et al., *J. of Poly. Sci: Part C: Polymer Letters* 28:187-191 (1990). Solid polymer electrolytes having anionic conductivity have been reported as well, see, e.g., Miyanishi et al., *Macromolecules* 17:975-977 (1984).

In solid electrolytic systems, single-ion conducting polymers provide a distinct advantage over dual-ion conducting polymers (wherein both the anion and cation have mobility in the electrolyte) in that they can charge and discharge more completely (in part because DC polarization does not occur). More particularly, single-ion conducting polymer electrolytes have the capability of exclusively transporting cations, such as lithium, thereby minimizing polarization effects at the electrodes. Further, single-ion conducting electrolytes avoid the condition wherein both the dissociated cation and anion of the metal salt dissolve in the electrolyte and move toward the positive and negative electrodes at the same time, reducing the ion transportation value.

A number of single-ion conducting electrolytes have been reported. Poly(ethylene oxide)-polyelectrolyte blends—consisting of PEO mixed with an acrylate polymer having pendant sulfonate or perfluorocarboxylate groups—have been described which exhibit a lithium ion transference number close to unity. See, e.g., Bannister et al., *Polymer* 25:1291-1296 (1984). A single-ion conducting solid polymer electrolyte system comprising a solid solution having ionic species dissolved therein has also been described in U.S. Pat. No. 5,102,751 to Narang et al., the disclosure of which is incorporated herein by reference. Further, a single-ion conducting polymer consisting of short PEO units functionalized by N-(fluoroalkylsulfonate)amido has been reported. See, e.g., Armand et al., (*Seventh International Meeting on Lithium Batteries*), May 15-20, 1994. However, each of the above-described single-ion conducting polymer systems generally exhibit low conductivity (e.g., $\sigma \leq 10^{-5}$ S/cm at 100° C.) as well as low electrochemical stability.

Accordingly, while the various solid polymer electrolytes set forth in the above publications have shown promise, those materials have limitations which prevent them from practical use in, for example, high energy-rechargeable batteries and other applications in which high ionic conductivity is necessary and wherein relatively thin films of the polymer electrolyte must be prepared. As noted above, prior polymer electrolytes do not exhibit sufficient ionic conductivity, particularly at room temperature. Further, such prior polymer electrolytes have generally not exhibited desirable physical properties for incorporation in electrolytic devices where, frequently, thin films of these electrolytes are necessary. For example, physical limitations inherent in those polymers include polymer films which may be too sticky, the polymers may be too close to being liquid, the polymers may be too brittle, or the polymers may be too heat sensitive.

One approach to overcoming some of the above-noted problems (i.e., brittleness, low ionic conductivity, and the like) with prior polymer electrolytes has been the combination of those electrolytes with liquid electrolytes that serve as plasticizers. In this manner, a number of plasticizers have been found to be useful in enhancing the ionic conductivity of solid polymer electrolytes. See, e.g., U.S. Pat. No. 5,102,751 to Narang et al., incorporated by reference above. Additionally, gel electrolytes containing poly(vinylidene fluoride) ("PVdF") have been developed, although such polymer electrolytes generally contain conventional lithium salts which are known to behave as dual-ion conductors, reducing the cation transport values obtainable from such systems. Further, gel electrolytes containing plasticizers have been reported (see, e.g., Tsuchida et al., *Electrochemical Acta* 28(5):591–595 (1983)); however, such electrolytes have been found to exhibit insufficiently high conductivity at room temperature. The use of PVdF copolymers to prepare gel electrolytes containing lithium salts has also been described by Gozdz et al. in U.S. Pat. No. 5,296,318; however, that method did not enable preparation of homogeneous, physically strong gel electrolyte films without phasic separation of the lithium salt.

Accordingly, although some prior plasticizers have been shown to improve conductivity in solid electrolyte polymers, those compositions still suffer from serious drawbacks. In particular, prior plasticizers have been found to be too volatile, causing them to separate from the polymer electrolyte composition over a period of time. Such separation results in a decrease in the conductivity, and further, the physical properties of the polymer will likewise change; for example, the polymer might become more brittle and/or might peel from a substrate on which it has been coated.

Other prior liquid electrolytes and plasticizers, such as propylene carbonate, are known to be reduced at the lithium anode or carbon anode of lithium batteries, therefore limiting battery performance. See, e.g., Arakawa et al., *J. Electroanal. Chem.* 219:273–280 (1987) and Shu et al., *J. Electrochem. Soc.* 140:922–927 (1993). The extent of propylene carbonate reduction is particularly severe on graphite electrodes. Although crown ethers have been used as additives in batteries to minimize such propylene carbonate reduction at the anode (see, e.g., Shu et al., *J. Electrochem. Soc.* 140:L101–L103 (1993) and U.S. Pat. No. 5,130,211 to Wilkinson et al.), high concentrations (0.3–0.5M) of crown ether are needed to adequately minimize electrolyte reduction. In this regard, since crown ethers are highly toxic and generally quite expensive, they are not expected to be of practical use in batteries.

Accordingly, there remains a need to provide single-ion conductive solid polymer electrolytes capable of exhibiting conductivities in the range of their liquid electrolyte counterparts at room temperature (e.g., in the range of a σ≧10⁻³ S/cm at 20° C.) as well as enhanced electrochemical stability. Additionally, there has remained a need to develop plasticizers for use with such polymer electrolytes that are capable of providing a plasticizing effect while also significantly enhancing the ionic conductivity of the solid polymer. Such plasticizers should not exhibit the drawbacks experienced by prior systems such as being readily volatilized away from the polymer and/or deleteriously altering the mechanical properties of the polymer.

The invention disclosed and claimed herein addresses the aforementioned deficiencies in the art by providing liquid electrolyte plasticizers which have a surprisingly enhanced ambient temperature conductivity. The novel plasticizers may be used as the electrolyte component of batteries or other electrochemical devices. In addition, when the liquid electrolyte plasticizers of the invention are formulated with solid polymer electrolytes a composition results having enhanced conductivity and which may be made into gels or films for use in batteries or other electrochemical devices.

SUMMARY OF THE INVENTION

Accordingly, it is a primary object of the invention to address the aforementioned need in the art by providing novel liquid electrolyte plasticizers having enhanced ambient temperature conductivity and which, when formulated with solid polymer electrolytes ("SPEs"), enhance the physical and mechanical attributes of the SPEs.

It is another object of the invention to provide such liquid electrolyte plasticizers having the structure $$R^a O-(OC_2R^b{}_4)_\alpha-(CO)_\beta-[O(X)_\gamma-R^c-(X)_\gamma-O-CO-]_l-(OC_2R^b{}_4)_\alpha-OR^a$$

wherein:

$R^a$ is independently selected from the group consisting of alkyl, $-(CO)OR^d$, $-(C_pH_{2p})_\tau-(OC_2R^b{}_4)_\alpha-OR^d$,

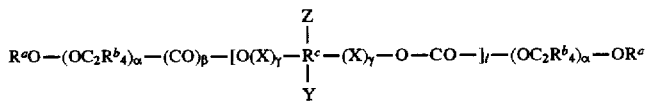, and

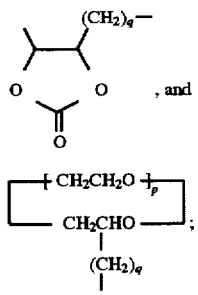;

$R^b$ is independently selected from the group consisting of H, alkyl, aryl, alkenyl, fluoro, and fluorinated lower alkyl;

$R^c$ is alkylene or $-(C_pH_{2p})_\tau-(OC_2R^b{}_4)_\alpha-$;

$R^d$ is H or alkyl;

X is lower alkylene;

Y is selected from the group consisting of H, aryl and alkyl;

Z is selected from the group consisting of H and $CH_2O(CO)OR^a$;

α, γ, l, ρ and τ are integers in the range of 0 to 10 inclusive;

β is 0, 1 or 2;

p is an integer in the range of 1 to 5 inclusive; and q is an integer in the range of 0 to 6 inclusive.

It is yet another object of the invention to provide a liquid electrolyte plasticizer having the structural formula

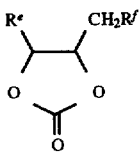

wherein:

$R^e$ is H, alkyl or —$CH_2OR^g$;

$R^f$ alkyl, —$(OC_2R^b{}_4)_\alpha$—$R^g$, —$(OC_2R^b{}_4)_\alpha$—$OR^g$, $OR^g$, or

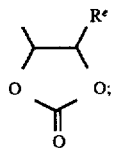

$R^g$ is H, alkyl, —$(OC_2R^b{}_4)_\alpha$—$R^h$ or

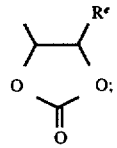

$R^h$ is H or alkyl; or wherein $R^e$ and $R^f$ may be linked through an alkylene or —$(OC_2R^b{}_4)_\alpha$— bridge, with $R^b$ defined as above.

It is a further object of the invention to provide a liquid electrolyte plasticizer having the structure

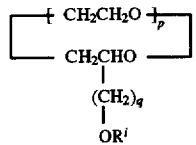

wherein:

$R^i$ is alkyl, —$(OC_2R^b{}_4)_\alpha$—$R^j$ or —$(CO)OR^j$;

$R^j$ is H, alkyl or —$(OC_2R^b{}_4)_\alpha$—$R^k$;

$R^k$ is H or alkyl; and $R^b$, p and q are defined as above.

The functionalized cyclic ethers have surfactant properties, low volatility, and can be covalently bound to a carbon electrode to prevent any possible leaching and, as such, may be used as battery electrolyte additives.

It is still another object of the invention to provide conductive compositions having enhanced ambient temperature conductivity containing a liquid electrolyte plasticizer as described herein, and, optionally, a high dielectric constant solvent and/or a salt of the formula C-A, wherein C is a cation including virtually any species which can bear a positive charge and includes the elements of Groups IA, IB, IIA, IIB, IIIA, IIIV, IVA, IVB, VA, VB, VIA, VIB, VIIA, VIIB, and VIII of the Periodic Table of Elements, and A is an anion which may be Cl, $CF_3SO_3$, $ClO_4$, $BF_4$, Br, I, SCN, $AsF_6$, $N(CF_3SO_2)_2$, $PF_6$, $SbF_6$, $O(CO)R^l$, wherein $R^l$ is H, alkyl, aryl, alkenyl, halo, haloalkyl, or the like.

It is still a further object of the invention to provide conductive compositions having enhanced ambient temperature conductivity wherein those compositions are formed from a combination of a liquid electrolyte plasticizer according to the present invention and, optionally, a solid polymer electrolyte, a high dielectric constant solvent and/or a salt of the formula C-A, wherein C and A are as defined above, or mixtures of SPEs, solvents or salts.

It is yet another object of the invention to provide conductive films which are generally formed from a combination of a liquid electrolyte plasticizer as described above, a salt of the formula C-A, a suitable amount of a strengthening material such as poly(vinylidene fluoride) in an amount effective to enhance the mechanical strength of the resulting electrolyte composition, and, optionally an SPE, and/or a high dielectric constant solvent. In this manner, the plasticizers of the present invention improve the conductivity and the physical properties of the composition in that they may be formulated in thin but nevertheless highly conducting films having desirable physical properties such as enhanced mechanical strength and lack of stickiness.

According to the invention, there is further described a method of manufacturing such conductive films and other conductive compositions. Generally, such a method will involve a hot press technique for forming films; however, depending on the amounts of various components incorporated into the compositions, waxes and gels may be prepared as well.

In one aspect of the invention, the liquid electrolyte plasticizers disclosed and claimed herein may be used in batteries, for example, a solid state $Li_xC_6/SPE/LiCoO_2$, $Li/SPE/TiS_2$ or $Li/SPE/V_6O_{13}$ battery, or in electrochemical devices such as fuel cells, supercapacitors, electrochromic devices and sensors or the like.

In another aspect of the invention, the liquid electrolyte plasticizers may be used in combination with solid polymer electrolytes in order to improve the conductivity and the physical properties of the SPE. When the liquid electrolyte plasticizers are formulated with a suitable SPE, solid electrolytes are provided having enhanced ambient temperature conductivities and excellent physical and mechanical attributes such as high flexibility, strength and electrochemical stability. Suitable SPEs, for example, single-ion conducting polymer electrolytes, are described in commonly assigned U.S. Pat. No. 5,061,581 to Narang et al., as well as in U.S. Pat. No. 5,548,055, entitled "Single-Ion Conducting Solid Polymer Electrolytes," inventors Narang et al., filed on even date herewith. The disclosures of both of the aforementioned documents are incorporated herein by reference.

In still another aspect of the present invention, the liquid electrolyte plasticizers may be used in the formulation of solid-state electrochemical devices such as fuel cells, supercapacitors, electrochromic devices and sensors, or in a battery such as in a solid state lithium battery or the like. In this regard, a solid-state battery comprising a positive electrode, a negative electrode and a liquid electrolyte plasticizer as described above is disclosed herein.

In yet a further aspect of the invention, the presently described liquid electrolyte plasticizers may be used in combination with SPEs to form thin film SPEs; and, optionally, PVdF may be added in order to improve the SPE film mechanical strength. Accordingly, there are also provided herein solid-state batteries comprising a positive electrode, a negative electrode and a SPE film according to the invention. With the subject SPE films, solid-state batteries such as a $Li_xC_6/SPE/LiCoO_2$ battery may be fabricated having enhanced conductivity and rechargability.

DETAILED DESCRIPTION OF THE INVENTION

Definitions

Figure 1:
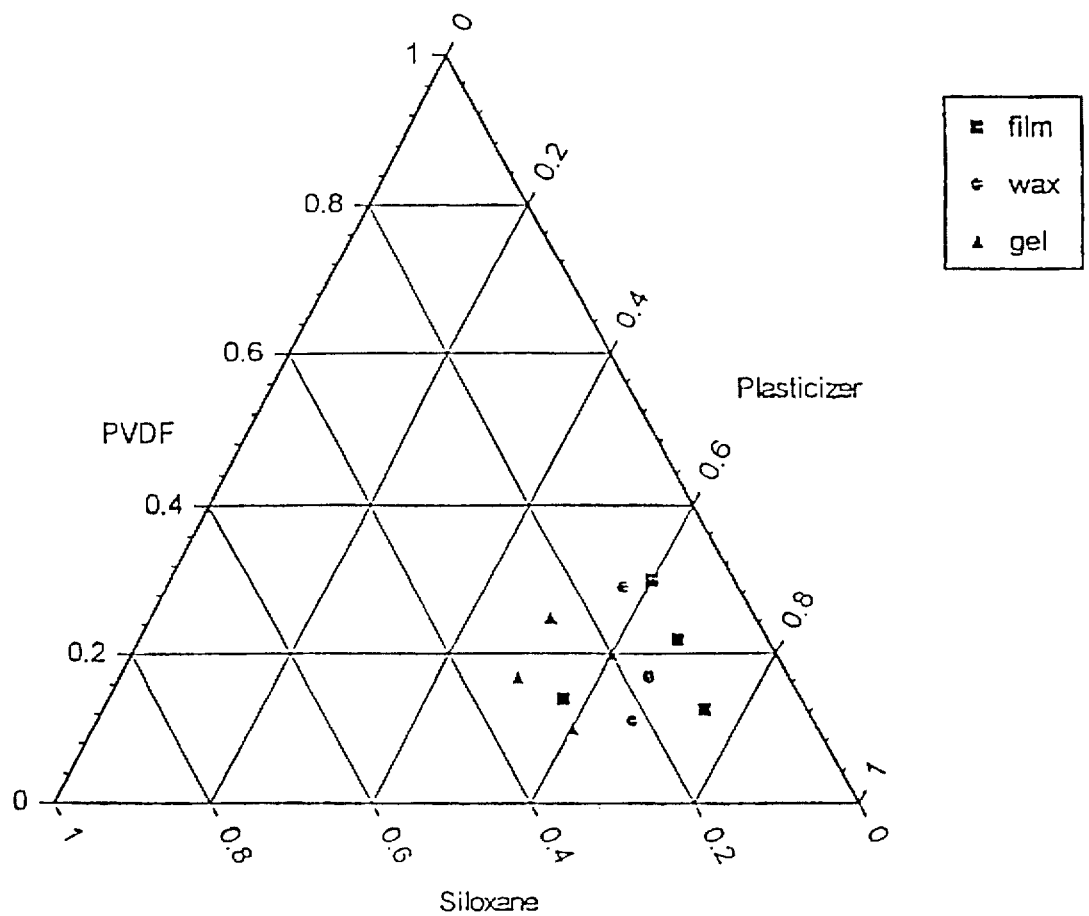
FIG. 1 is a diagram illustrating ranges of components in a composition containing a single-ion conduction solid polymer electrolyte, a plasticizer and PVdF, for forming films, waxes and gels.

Before describing the present invention in detail, it is to be understood that this invention is not limited to particular salts, methods of synthesis, solvents, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the content clearly dictates otherwise. Thus, for example, reference to "a high dielectric constant solvent" includes mixtures of such solvents, reference to "a plasticizer" includes mixtures of plasticizers, and the like.

In this specification and in the claims which follow, reference will be made to a number of terms which shall be defined to have the following meanings:

The term "polymer" is intended to include both oligomeric and polymeric species, i.e., compounds which include two or more monomeric units, which may be a homopolymer or a copolymer. When a single generic structure is shown, e.g., as in formula (I), it is to be understood that the polymers described may contain two or more different monomeric units represented by the single generic structure. A "conductive polymer" is one which possesses conducting as opposed to insulating electrical-transport properties.

The term "homopolymer" intends a polymer incorporating a single species of monomer units. By contrast, the term "copolymer" refers to a polymer constructed from two or more chemically distinct species of monomer units in the same polymer chain. A "block copolymer" is a polymer which incorporates two or more segments of two or more distinct species of homopolymers or copolymers.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms. The term "fluorinated lower alkyl" intends an alkyl group of one to six carbon atoms in which at least one hydrogen atom, and optionally all hydrogen atoms, are replaced with fluorine atoms.

The term "alkenyl" refers to a branched or unbranched hydrocarbon chain containing from 2 to 24 carbon atoms and at least one double bond. "Lower alkenyl" refers to an alkenyl group of 2 to 6, more preferably 2 to 5, carbon atoms. The term "fluorinated lower alkenyl" intends an alkenyl group of one to six carbon atoms in which at least one hydrogen atom, and optionally all hydrogen atoms, are replaced with fluorine atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "aryl" as used herein refers to a monocyclic aromatic species of 5 to 7 carbon atoms, and is typically phenyl. Optionally, these groups are substituted with one to four, more preferably one to two, lower alkyl, lower alkoxy, hydroxy, and/or nitro substituents.

The term "aralkylene" is used to refer to moieties containing both alkylene and monocyclic aryl species, typically containing less than about 12 carbon atoms in the alkylene portion, and wherein the aryl substituent is bonded to the structure of interest through an alkylene linking group. Exemplary aralkylene groups have the structure —(CH$_2$)$_j$—Ar wherein j is an integer in the range of 1 to 6.

"Halo" or "halogen" refers to fluoro, chloro, bromo or iodo, and usually relates to halo substitution for a hydrogen atom in an organic compound. "Haloalkyl" refers to an alkyl moiety in which one or more of the hydrogen atoms is substituted by a halo atom. Of the halos, fluoro is generally preferred. The term "lower haloalkyl" intends an alkyl group of one to six carbon atoms in which at least one hydrogen atom, and optionally, all hydrogen atoms, are replaced with halogen atoms.

"Optional" or "optionally" means that the subsequently described circumstance may or may not occur, and that the description includes instances where said circumstance occurs and instances where it does not. For example, the phrase "optional covalent bond" means that a covalent bond may or may not be present and that the description includes both the instance when the covalent bond is present and the instance when the covalent bond is not present.

The Novel Compounds

In one embodiment of the invention, there are provided a number of liquid electrolyte plasticizers. More particularly, there are provided liquid electrolyte plasticizers represented by the general formula

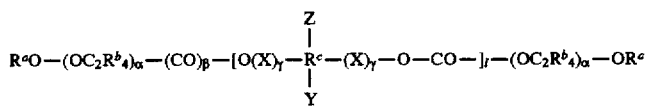

wherein $R^a$, $R^b$, $R^c$, X, Y, Z, $\alpha$, $\beta$, $\gamma$, and l are as defined above. Preferably $R^b$ is H or fluoro. Preferred embodiments of this group of compounds include $R^a$—(OC$_2$R$^b_4$)$_\alpha$—(CO)—O—CH$_2$—CH$_2$—O—(CO)—(OC$_2$R$^b_4$)$_\alpha$—$R^a$ and $R^a$O—(OC$_2$R$^b_4$)$_\alpha$(CO)—(OC$_2$R$^b_4$)$_\alpha$—OR$^a$, wherein $R^a$ is lower alkyl, or

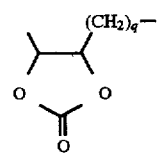

There are further provided liquid electrolyte plasticizers represented by the general formula

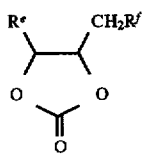

wherein $R^e$ and $R^f$ are as defined above.

There are further provided liquid electrolyte plasticizers represented by the general formula

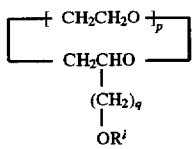

wherein $R^i$, p and q are as defined above.

Specific examples of preferred liquid electrolyte plasticizers are set forth in Table I:

TABLE I

STRUCTURES OF ELECTROLYTE PLASTICIZERS

| NUMBER | PLASTICIZER |
|---|---|
| P1 | $CH_2OCH_2CH_2OCH_2CH_2OCH_3$ (cyclic carbonate) |
| P2 | $CH_2OCH_2CH_2OCH_3$ (cyclic carbonate) |
| P3 | $CH_2OCH_2CF_2CF_2CF_3$ (cyclic carbonate) |
| P4 | $CH_2OCH_2CH_2OCH_2$ (bis cyclic carbonate) |
| P5 | $CH_2O(CH_2CH_2O)_2CH_2$ (bis cyclic carbonate) |
| P6 | $CH_2\text{--}CH_3$ (bis cyclic carbonate) |
| P7 | $CH_2OC_2H_4OC_2H_4OCH_3$ (dioxolane-type) |

TABLE I-continued

STRUCTURES OF ELECTROLYTE PLASTICIZERS

| NUMBER | PLASTICIZER |
|---|---|
| P8 | $CH_2OCOCH_2C$ (bis-dioxolane) |
| P9 | $CH_2OCOC_2H_5$ (cyclic carbonate) |
| P10 | $CH_3CCH_2OCOC_2H_5$ with three $CH_2OCOC_2H_5$ groups |
| P11 | $CH_3C(OC_2H_5)_3$ |
| P12 | $CHC(OC_2H_5)_3$ |
| P13 | $(CH_3OC_2H_4O)_2CO$ |
| P14 | $(CH_3(OC_2H_4)_2O)_2CO$ |
| P15 | $(C_2H_5OC_2H_4O)_2CO$ |
| P16 | $(CH_3(OC_2H_4)_2O(CO))_2$ |
| P17 | $(CH_3CH_2O(CO)OCH_2)_2$ |
| P18 | $(CH_3O(CO)OCH_2)_2$ |
| P19 | $(CH_3O(CO)OCH_2CH_2)_2O$ |

The liquid electrolyte plasticizers of the invention may be prepared using conventional techniques well-known to those skilled in the art of synthetic organic chemistry or which may be found in the relevant texts such as in Kirk-Othmer's *Encyclopedia of Chemical Technology*, in House's *Modern Synthetic Reactions*, in C. S. Marvel and G. S. Hiers' text *ORGANIC SYNTHESIS*, Collective Volume 1, or the like. Synthesis of representative plasticizers is exemplified below in Schemes I and II:

SCHEME I $$HOCH_2CH_2OH + 2\,R^a\text{---}(OC_2R^b{}_4)_\alpha\text{---}CO\text{---}Cl \xrightarrow[THF]{Pyridine}$$

$$R^a\text{---}(OC_2R^b{}_4)_\alpha\text{---}CO\text{---}O\text{---}CH_2\text{---}CH_2\text{---}O\text{---}CO\text{---}(OC_2R^b{}_4)_\alpha\text{---}R^a$$

SCHEME II $$2\,R^aO\text{---}(OC_2R^b{}_4)_\alpha\text{---}OH + R^m{}_2\text{---}CO \xrightarrow[\Delta]{benzene}$$

$$R^aO\text{---}(OC_2R^b{}_4)_\alpha\text{---}CO\text{---}(OC_2R^b{}_4)_\alpha\text{---}OR^a$$

wherein $R^a$ and $R^b$ are as defined above, and $R^m$ is imidazole or the like.

The compounds are electrochemically stable from 0 V to 4.5 V versus a lithium reference electrode. In addition, the novel liquid electrolyte plasticizers have enhanced ambient temperature conductivity (see Table II). Consequently, these novel compounds may serve as the electrolyte component of batteries having positive and negative electrodes, or may be used in conjunction with other electrochemical devices.

The novel electrolyte plasticizers may be formulated with a salt of the formula C-A, defined as above, wherein C is preferably lithium or sodium, (e.g., LiPF$_6$, LiAsF$_6$, LiN(SO$_2$CF$_3$)$_2$, and the like) and a high dielectric constant solvent such as ethylene carbonate, propylene carbonate, dimethyl carbonate, diethoxyethane, diethyl carbonate, dimethoxyethane, dipropyl carbonate, methoxyethoxy ethyl ether, or mixtures thereof. Such formulations have been shown to have conductivities at room temperature higher than 5×10$^{-3}$ S/cm (see Table 2).

In addition to having enhanced ambient temperature conductivity, the novel liquid electrolyte plasticizers may serve as plasticizers of polymer electrolytes and thereby adjust the mechanical properties of the polymer electrolytes. Additionally, the liquid electrolyte plasticizers increase the conductivity of polymer electrolytes. Polymer electrolytes/plasticizers formulations may be prepared to contain about 5 wt. % to 95 wt. % polymer, preferably about 10 wt. % to 50 wt. %, most preferably about 10 wt. % to about 25 wt. %.

The types of solid polymer electrolytes which can have their conductivity increased, often by as much as three orders of magnitude, include: 1) those which carry a negative charge and have a positively charged ionic species associated with them; 2) those which carry a positive charge and have a negatively charged ionic species associated with them; 3) those which are solid solutions having ionic species dissolved therein; and 4) those which are covalently functionalized with a moiety carrying an ionic species.

Examples of polymers useful as solid polymer electrolytes for purposes of the present invention include polyethers, polyesters, polyethylene oxides, poly(ethylene) imine, polyphosphazenes, polysiloxane, partially fluorinated polymethacrylates, or such polymers modified to include functionalized chains, e.g., alkylsulfonates, or the like. Such polymers can be synthesized by methods well known in the art or can be obtained commercially. The polymer backbone may also include copolymers of two or more polymers with repeating units of individual monomers.

Some examples of solid polymer electrolytes which carry a negative charge and have a positively charged ionic species associated with them are described in U.S. Pat. No. 5,102,751 to Narang et al., incorporated by reference above. Examples of solid polymer electrolytes which are covalently functionalized with a moiety carrying an ionic species include those described in U.S. Pat. No. 5,548,055 inventors Narang et al., also incorporated by reference above.

The SPEs which are specifically contemplated for use herein include single-ion conducting polymers having the structure as shown in Formula (I)

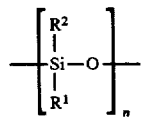  (I)

wherein:

R$^1$ and R$^2$ are individually selected from the group consisting of moieties having the structure

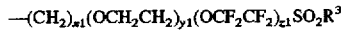

in which R$^3$ is —OM, —N(M)SO$_2$CF$_3$ or —C(M)(SO$_2$CF$_3$)$_2$ and M is an alkali metal, or wherein one of R$^1$ and R$^2$ has the structure

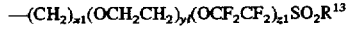

and the other is selected from the group consisting of hydrogen, lower alkyl, lower halo alkyl, lower alkenyl, fluorinated lower alkenyl, aryl and aralkylene;

x1 and z1 may be the same or different and are integers in the range of 1 to 100 inclusive;

y1 is an integer in the range of 0 to 100 inclusive; and n is an integer indicating the number of mer units in the polymer.

Additional SPEs contemplated for use herein include single-ion conducting co-polymers which contain first mer units having the structure as shown in Formula (II)

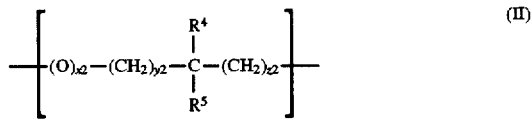  (II)

and second mer units having the structure as shown in Formula (III)

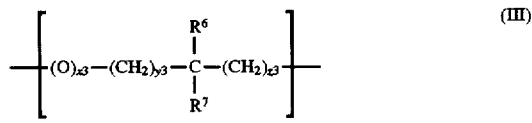  (III)

wherein:

R$^4$ and R$^6$ are independently selected from the group consisting of hydrogen, lower alkyl, lower alkoxy, —COOR$^8$ and —(CH$_2$)$_{n1}$—O—R$^8$ in which R$^8$ is lower alkyl or fluorinated lower alkyl and n1 is an integer in the range of 1 to 6 inclusive;

R$^5$ is —(CH$_2$)$_{x4}$(OCH$_2$CH$_2$)$_{y4}$(OCF$_2$CF$_2$)$_{z4}$SO$_2$M in which M is an alkali metal;

R$^7$ is —(CH$_2$)$_{x5}$(OCH$_2$CH$_2$)$_{y5}$OCH$_3$ or —COOR$^9$ in which R$^9$ is lower alkyl or fluorinated lower alkyl; and x2, x3, x4, x5, y2, y3, y4, y5, z2, z3 and z4 may be the same or different and are integers in the range of 1 to 100 inclusive.

Mechanically strong electrolyte films which have conductivities higher than 10$^{-3}$ S cm$^{-1}$ may be formed from a combination of a liquid electrolyte plasticizer as disclosed and claimed herein or mixtures of such plasticizers, a strengthening material such as PVdF, a salt of the formula C-A, and, optionally, a solid polymer electrolyte and/or a high dielectric constant solvent such as propylene carbonate ("PC"), ethylene carbonate ("EC"), dimethoxyethane ("DME"), methoxyethoxy ethyl ether ("MEE"), and the like (see Table III). Preferably C-A is a lithium salt and the solid polymer electrolyte is a single-ion conductor polymer electrolyte as disclosed in U.S. Pat. No. 5,548,055 incorporated by reference above. It may be necessary to add a glyme (e.g., dimethoxyethane (C$_4$H$_{10}$O$_2$), diglyme (C$_6$H$_{14}$O$_3$), triglyme (C$_8$H$_{18}$O$_4$), tetraglyme (C$_{10}$H$_{22}$O$_5$) or so on) to form a homogeneous blend of the SPE with PVdF; such compounds will typically serve not only as solvents but as additional plasticizing agents as well.

Manufacturing Methods

A preferred method of manufacturing conductive compositions containing the novel liquid electrolyte plasticizers is a hot-press technique for forming films. Such a method typically involves: (a) forming a gel electrolyte composition by combining (i) a single-ion conducting SPE (e.g., a polysiloxane of Formula (I) or a copolymer containing mer units (II) and (III)), with (ii) an effective amount of liquid electrolyte plasticizer according to the invention for enhancing the ionic conductivity of that SPE and (iii) an amount of PVdF or an alternative material effective to enhance the mechanical strength of the composition; (b) heating the resulting combination at a temperature and for a time effective to form a fluid solution; (c) pressing the fluid solution; (d) cooling the solution; and (e) releasing the film so provided.

If waxes or gels are preferred, rather than films, the relative quantities of components can be adjusted to provide these alternative forms of conductive compositions. Reference may be had to FIG. 1, in which it may be seen that compositions containing less electrolyte will generally form a gel, compositions containing slightly more electrolyte will generally form a wax, and compositions containing even more electrolyte will form a film. Alternative methods of manufacturing such conductive compositions will be readily apparent to those skilled in the art, or may be deduced from the relevant literature.

Industrial Applicability

Conductive compositions formulated with the novel liquid electrolyte plasticizers are useful in a variety of contexts. An important utility is in the fabrication of batteries. Solid-state batteries formulated with the novel electrolyte plasticizers comprise a positive electrode, or anode, a negative electrode, or cathode, and the liquid electrolyte plasticizer. The anode is usually a carbon-based material such as petroleum coke or graphite. Alternatively, lithium metal may be used as the anode, or intercalating metal oxides such as tungsten or iron oxides. The cathode is generally of a lithium-containing material such as $LiCoO_2$, $LiMn_2O_4$ or $LiNiO_2$; however, alternative materials could be used as well, e.g., $V_6O_{13}$.

It will be appreciated that conductive compositions formulated with the novel electrolyte materials of the invention are also useful in the fabrication of fuel cells, sensors, supercapacitors, electrochromic devices, and the like, using manufacturing techniques well known to those skilled in the art, or readily available in the relevant literature.

The following examples are intended to provide those of ordinary skill in the art with a complete disclosure and description of how to make and use the novel liquid electrolyte plasticizers of the invention, and are not intended to limit the scope of what the inventors regard as their invention in any way. Efforts have been made to ensure accuracy with respect to numbers used (e.g., amounts, temperatures, etc), but some experimental error and deviation should, of course, be allowed for. Unless indicated otherwise, parts are parts by weight, temperatures are in degrees centigrade, and pressure is at or near atmospheric.

Experimental
Equipment and Measurement Technique

Conductivities of the electrolytes and electrolyte compositions and films made therewith were evaluated by AC impedance spectroscopy. For example, a film of the dried polymer electrolyte was sandwiched between two stainless steel blocking electrodes that each had an area of 0.7854 $cm^2$. The thickness of the polymer film, which typically varied between 0.51 mm and 1.02 mm, was measured with a micrometer. The assembly, composed of the blocking electrode-polymer sandwich cell inside a DELRIN® (a polyacetal resin available under the trademark DELRIN® from E. I. Du Pont De Nemours and Company, Wilmington, Del.) cup, was transferred to a vacuum chamber that had provision for heating and for applying a constant pressure of 65-97 $lb/in_2$ across the polymer film. The electrodes were connected to a potentiostat (PAR 173) operating in the galvanostatic mode.

The cell was then perturbed with a small AC signal generated by a Solartron 1250 Frequency Response Analyzer, and the real and imaginary components of the cell impedance were measured as a function of frequency at each of the desired temperatures. The setup was allowed to stabilize overnight after the temperature was changed. The AC impedance data were plotted in both the Nyquist and Bode planes to identify the high frequency relaxation arising due to the polymer electrolyte. Typically, the frequency of the AC signal was scanned from 65 KHz down to 10 mHz. The intercept at the real axis of the high frequency relaxation was assumed to represent the resistive component of the polymer electrolyte impedance. This was then converted to the resistivity of the polymer (the thickness and the area of the polymer film were known). The reciprocal of resistivity gave the conductivity, σ, having units of $\Omega^{-1}$ $cm^{-1}$. In cases where high frequency relaxation occurred above 65 KHz, a Hewlett Packard 4192A Impedance Analyzer was used to measure the polymer electrolyte resistance. This instrument has a frequency range capability of 13 MHz to 5 Hz.

The battery performance tests utilized a PAR 173 potentiostat/galvanostat to produce constant current charge/discharge cycles between predetermined voltage levels.

Preparation of Polymer Films

Method A: Solutions of plasticizer- and polymer-containing films were prepared by dissolving a known quantity of plasticizer and polymer in a dry solvent. For conductivity measurements, the polymer solution was added drop-wise into the DELRIN® cup to cast a film. The film was then dried for 3 days in a glass vacuum apparatus at 120° C. at<0.01 torr. Film thickness was measured using a micrometer.

Method B: An alternative method by which films having a selected thickness may be prepared generally comprises the steps of (a) forming a gel electrolyte composition by combining (i) a single-ion conducting SPE with (ii) an effective amount of plasticizer for enhancing the ionic conductivity of that SPE and (iii) an effective amount of PVdF for enhancing the mechanical strength of the composition and heating the resulting combination at about 120° C. for about 15 minutes to form a fluid solution; and (b) pressing the fluid solution between MYLAR® (a polyester film available under the trademark MYLAR® from E. I. Du Pont De Nemours and Company, Wilmington, Del. sheets spaced apart by spacer means having a selected thickness and cooling the fluid solution whereby a mechanically strong single-ion conducting gel electrolyte film is provided.

Preparation and Testing of Batteries

Materials: All procedures for handling the cell materials were conducted in a nitrogen dry box. Batteries containing Li metal were assembled in an argon dry box to prevent any reaction of lithium with nitrogen to form lithium nitride.

Tetrahydrofuran (THF) was distilled from Na/benzophenone under nitrogen before use. Chloroform was distilled from calcium hydride under nitrogen. Acetonitrile was distilled from $P_2O_5$. Lithium trifluoromethanesulfonate ($LiCF_3SO_3$) obtained from Aldrich Chemical was used as received. Lithium ribbon (0.38 mm thick×50 mm wide) was obtained from AESAR Ward Hill, Mass. and stored under argon. Ammonium vanadate (Aldrich Chemical Co., 99.99%) was used without further purification. Shawinigan black (50% compressed) was obtained from Chevron Chemical Co., $MoS_2$ cathodes produced by chemical vapor deposition (CVD) on an aluminum substrate were obtained from Polytechnic University, Brooklyn, NY. Polyethylene oxide (PEO, MW=100,000) was obtained from Aldrich Chemical Co. and dried at 140° C. before use.

Preparation of Liquid Electrolyte Plasticizer-Polymer Complexes: Solutions of liquid electrolyte plasticizer and polymer complexes were prepared by dissolving a known quantity of plasticizer and polymer in dry solvent. Mixtures of plasticizers and polymers contain about 5 wt. % to 95 wt. % polymer, preferably about 10 wt. % to 50 wt. %, most preferably about 10 wt. % to about 25 wt. %. Optionally, a lithium salt was added (e.g., LiCF$_3$SO$_3$). The mixture was allowed to stand overnight.

A typical electrolyte formulation contained 10–25% polymer (e.g., PVdF), 10–15% lithium salt and 67–75% plasticizer/high dielectric constant solvent solution. The mixture was heated at about 120° C. for 15 minutes. The fluid-hot solution was pressed between MYLAR® sheets, and upon cooling a dense strong solid electrolyte film was formed. Alternatively, vinylidene fluoride may be polymerized in situ in the presence of polymer electrolyte and plasticizer.

For conductivity measurements, the solution was added drop-wise into the DELRIN® cup to cast a film. The film was then dried for 3 days in a glass vacuum apparatus at 120° C. at<0.01 torr. Film thickness was measured using a micrometer.

For battery tests, the solvent from the plasticizer/polymer complex was allowed to evaporate in the dry box. The complex was then transferred to the DELRIN® cup and vacuum dried as describe above.

Preparation of V$_6$O$_{13}$ Cathodes: Vanadium oxide was prepared by thermally decomposing ammonium vanadate in argon. NH$_4$VO$_3$ was placed in a quartz boat and flushed with argon for 30 minutes. The temperature was then raised from room temperature to 500° C. at a rate of 4° C./min. After 1 hour at 500° C., the temperature was raised to 550° C. at a rate of 4° C./min., held at 55° C. for 1 hour and then slowly cooled to room temperature. The product obtained was dark blue in color.

The composition of the cathode was 80% V$_6$O$_{13}$, 5.5% Shawinigan black, and 14.5% plasticizer/polymer complex by weight. The amounts of V$_6$O$_{13}$ and Shawinigan black required were weighed into a polycarbonate vial and ground for 5 minutes in a Wig-L-Bug grinder. The mixture was dried for 3 days at 140° C. and<0.1 torr in and Abderhalden drying apparatus. In a 3 ml vial, 100 mg of plasticizer/polymer complex was mixed with 589.7 mg of V$_6$O$_{13}$/Shawinigan black in THF. The mixture was intermittently shaken and allowed to stand overnight before the solvent was evaporated off in the dry box. The cathode mixture (100 mg) was pressed at 10,000 lb. for 3 minutes in a stainless steel die with area of 1.69 cm$^2$.

Battery Assembly: MoS$_2$ and V$_6$O$_{13}$ cathodes were cut to size with a 1 cm diameter punch. The cathodes were attached to the stainless steel plate in the Delrin® cup with conducting epoxy (Cho-Bond 584). The adhesive was cured at 120° C. for 1 hour. Approximately 100 mg of the plasticizer/polymer complex was weighed into the cup to form a film, as described above. Lithium anodes were freshly prepared by cutting lithium ribbon with the same punch and sanding the surfaces with emery paper. The cup was then loaded into the cell assembly.

EXAMPLE 1

Synthesis of CH$_3$CH$_2$—O—(CO)—O—CH$_2$—CH$_2$—O—(CO)—O—CH$_2$CH$_3$

Method A: To a solution of anhydrous ethylene glycol (31.0 g, 0.50 mol), pyridine (94.9 g, 1.20 mol) and THF (250 ml), ethyl chloroformate (119.5 g, 1.10 mol) was added drop-wise at 0° C. during a period of 30 min. The resulting white cloudy solution was allowed to be stirred for 30 min at 0° C. then for additional 16 hours at room temperature. The white precipitate was filtered off and washed with small amount of ether (3×50 ml). The clear solution was concentrated in a rotary evaporator, then washed with water (3×200 ml). The crude product was taken in ether (150 ml) and washed with brine and dried over MgSO$_4$. The MgSO$_4$ was filtered off and the filtrate was concentrated. The crude product 93 g was purified by vacuum fractional distillation (78°–83° C./0.07 mm Hg) to five clear liquid product 84.5 g (yield 82%). H$^1$ NMR (CDCl$_3$, d): 1.32 (t, 3H, CH$_3$CH$_2$O—), 4.21 (q, 2H, CH$_3$CH$_2$O—), 4.36 (s, 2H, —O(CO)OCH$_2$—). The product purity of the biscarbonate was confirmed by gas chromatography.

Method B: An alternative synthetic method is as follows.

In the absence of solvent, 1 equivalent of ethylene glycol, 4 equivalents of ethylchloroformate and 3 equivalents of solid sodium carbonate were added and initially mixed at 0°–5° C.; the mixture was then stirred overnight at room temperature. The excess ethylchloroformate was removed under reduced pressure and the pure biscarbonate product was recovered by extraction with ether, toluene or any other solvent in which biscarbonate is soluble. After solvent distillation, about 72% yield of biscarbonate and 12% yield of ethylene carbonate was obtained. The two may be separated by distillation if desired.

EXAMPLE 2

Synthesis of CH$_3$O(CH$_2$CH$_2$O)$_2$CH$_2$CH$_2$O(CO)OCH$_2$CH$_2$(OCH$_2$CH$_2$)$_2$OCH$_3$ A mixture of triethylene glycol monomethyl ether (8.5 g, 50 mmol) and 1,1'-carbonyl diimidazole (4.13 g, 25 mmol) in 50 ml benzene was refluxed with mixing at 85° C. for 48 hours. The mixture eas then diluted with 100 ml benzene. This mixture was extracted with water (2×100 ml), dried over Na$_2$SO$_4$, filtered and concentrated to yield 0.5 gm of colorless product.

The aqueous extracts were saturated with Nacl and extracted with CH$_2$C$_{12}$ (2×100 ml). The CH$_2$Cl$_2$ extracts were pooled, dried over MgSO$_4$, filtered and concentrated to yield 4.7 g of colorless product.

The products were analyzed by thin layer chromatography ("TLC") on a silica plate which was developed in ethyl acetate:methanol (95:5). A TLC analysis of the CH$_2$Cl$_2$ extracts of the water soluble product showed three spots corresponding to: (1) the product remaining after the aqueous extract; (2) unreacted triethylene glycol monomethyl ether; and (3) a third component which was determined by $^1$H-NMR to be the desired product.

EXAMPLE 3

Preparation of Liquid Electrolyte Plasticizer Compositions having Enhanced Conductivity Mixtures of the new plasticizers with the optional addition of a high dielectric constant liquid were used to make electrochemically stable highly conducting gel electrolytes. These same mixtures may be used as plasticizers of SPEs. Mixtures of plasticizers and polymers include about 5 wt. % to 95 wt. % polymer, preferably about 10 wt. % to 50 wt. %, most preferably about 10 wt. % to about 25 wt. %. Optionally, a lithium salt was added. The mixture was allowed to stand overnight. A typical electrolyte formulation contained 10–25% polymer (e.g., PVdF), 10–15% lithium salt and 67–75% plasticizer/high dielectric constant solvent solution.

Table II lists the experimentally determined conductivities of these liquid electrolyte plasticizers formulated with lithium salts as shown, in the absence or presence of high dielectric constant solvent or solvent mixtures.

TABLE II

| PLASTI-CIZER | SOLVENT | PLASTI-CIZER: SOLVENT | SALT (1.0M) | σ ($\Omega^{-1}cm^{-1}$) |
|---|---|---|---|---|
| P1 | — | — | $LiAsF_6$ | $9.33 \times 10^{-5}$ |
| P2 | — | — | $LiAsF_6$ | $3.11 \times 10^{-4}$ |
| P3 | — | — | $LiAsF_6$ | $1.50 \times 10^{-5}$ |
|  | — | — | $LiN(CF_3SO_2)_2$ | $2.64 \times 10^{-5}$ |
|  | EC | 1:1 | $LiN(CF_3SO_2)_2$ | $6.12 \times 10^{-4}$ |
| P4 | MEE | 1:1 | $LiN(CF_3SO_2)_2$ | $8.47 \times 10^{-4}$ |
|  | EC | 1:1 | $LiN(CF_3SO_2)_2$ | $4.07 \times 10^{-4}$ |
|  | EC:MEE (1:1) | 1:1 | $LiN(CF_3SO_2)_2$ | $5.69 \times 10^{-4}$ |
|  | EC:MEE (1:1) | 1:2 | $LiN(CF_3SO_2)_2$ | $1.40 \times 10^{-3}$ |
| P5 | — | — | $LiN(CF_3SO_2)_2$ | $8.86 \times 10^{-6}$ |
|  | EC | 1:1 | $LiN(CF_3SO_2)_2$ | $6.13 \times 10^{-4}$ |
| P6 | MEE | 1:1 | $LiN(CF_3SO_2)_2$ | $7.22 \times 10^{-4}$ |
|  | EC | 1:1 | $LiN(CF_3SO_2)_2$ | $4.03 \times 10^{-4}$ |
| P7 | — | — | $LiN(CF_3SO_2)_2$ | $1.00 \times 10^{-4}$ |
|  | EC | 1:1 | $LiN(CF_3SO_2)_2$ | $1.34 \times 10^{-4}$ |
| P8 | EC | 1:1 | $LiN(CF_3SO_2)_2$ | $6.13 \times 10^{-4}$ |
| P9 | EC | 1:1 | $LiN(CF_3SO_2)_2$ | $7.60 \times 10^{-4}$ |
| P10 | EC | 1:1 | $LiN(CF_3SO_2)_2$ | $5.65 \times 10^{-4}$ |
| P11 | EC | 1:1 | $LiN(CF_3SO_2)_2$ | $1.00 \times 10^{-4}$ |
| P12 | EC | 1:1 | $LiN(CF_3SO_2)_2$ | $1.82 \times 10^{-4}$ |
| P13 | — | — | $LiN(CF_3SO_2)_2$ | $5.37 \times 10^{-4}$ |
|  | EC | 1:1 | $LiN(CF_3SO_2)_2$ | $5.37 \times 10^{-4}$ |
| P14 | — | — | $LiN(CF_3SO_2)_2$ | $3.40 \times 10^{-4}$ |
|  | EC | 1:1 | $LiN(CF_3SO_2)_2$ | $9.10 \times 10^{-4}$ |
|  | — | — | $LiN(CF_3SO_2)_2$ | $2.34 \times 10^{-4}$ |
|  | EC | 1:1 | $LiN(CF_3SO_2)_2$ | $1.39 \times 10^{-3}$ |
| P15 | EC | 1:1 | $LiN(CF_3SO_2)_2$ | $1.48 \times 10^{-3}$ |
|  | EC | 1:3 | $LiPF_6$ (1.2 M) | $1.93 \times 10^{-3}$ |
|  | EC | 1:4 | $LiPF_6$ (1.2 M) | $2.20 \times 10^{-3}$ |
|  | EC:TrG | 1:4:1.7 | $LiPF_6$ (1.2 M) | $3.59 \times 10^{-3}$ |
| P16 | — | — | $LiN(CF_3SO_2)_2$ | $3.24 \times 10^{-4}$ |
|  | EC | 1:1 | $LiN(CF_3SO_2)_2$ | $1.47 \times 10^{-3}$ |
| P17 | — | — | $LiN(CF_3SO_2)_2$ | $1.76 \times 10^{-4}$ |
|  | EC | 1:1 | $LiN(CF_3SO_2)_2$ | $8.00 \times 10^{-4}$ |
|  | EC | 1:2.6 | $LiN(CF_3SO_2)_2$ | $1.89 \times 10^{-3}$ |
|  | EC | 1:3 | $LiPF_6$ (1.2 M) | $2.01 \times 10^{-3}$ |
|  | EC | 1:4 | $LiPF_6$ (1.2 M) | $2.60 \times 10^{-3}$ |
|  | EC | 1:5 | $LiPF_6$ (1.2 M) | $2.74 \times 10^{-3}$ |
|  | EC:MEE | 1:5:2 | $LiPF_6$ (1.2 M) | $4.45 \times 10^{-3}$ |
|  | EC:MEE | 1:5:6 | $LiPF_6$ (1.2 M) | $3.23 \times 10^{-3}$ |
|  | EC:TrG | 1:5:2 | $LiPF_6$ (1.2 M) | $5.10 \times 10^{-3}$ |
|  | EC:TrG | 1:3:2 | $LiPF_6$ (1.2 M) | $3.25 \times 10^{-3}$ |
|  | EC:TeG | 1:4:1.7 | $LiPF_6$ (1.2 M) | $4.33 \times 10^{-3}$ |
|  | EC:TeG | 1:5:2 | $LiPF_6$ (1.2 M) | $5.18 \times 10^{-3}$ |
| P18 | EC | 1:1 | $LiN(CF_3SO_2)_2$ | $1.38 \times 10^{-3}$ |
| P19 | EC | 1:1 | $LiN(CF_3SO_2)_2$ | $1.53 \times 10^{-3}$ |

In Table II, the abbreviations are as follows: EC, ethylene carbonate; MEE, methoxyethoxy ethyl ether; TrG, triglyme ($C_8H_{18}O_4$); and TeG, tetraglyme ($C_{10}H_{22}O_5$). It may be seen that high ambient temperature conductivity may be achieved and varied, if desired, by choosing different high dielectric constant solvents or and plasticizers, or varying the amounts thereof.

Table III lists the experimentally determined conductivities of films made with various liquid electrolyte plasticizers.

TABLE III

| Polymer Composition | $(CH_3CH_2O(CO)OCH_2)_2$: Solvent | σ ($\Omega^{-1}cm^{-1}$) |
|---|---|---|
| 11% $LiPF_6$ (1.10M) 22% PVdF 67% $(CH_3CH_2O(CO)OCH_2)_2$:EC | 1:4 | $1.04 \times 10^{-3}$ |
| 11% $LiPF_6$ (1.08M) 20% PVdF 69% $(CH_3CH_2O(CO)OCH_2)_2$:EC | 1:4 | $1.28 \times 10^{-3}$ |
| 14% $LiPF_6$ (1.44M) 22% PVdF 64% $(CH_3CH_2O(CO)OCH_2)_2$:EC | 1:3 | $1.27 \times 10^{-3}$ |
| 11% $LiPF_6$ (1.10M) 22% PVdF 67% $(CH_3CH_2O(CO)OCH_2)_2$:EC:TrG | 1:4:2 | $3.51 \times 10^{-3}$ |

*The two-component $(CH_3CH_2O(CO)OCH_2)_2$:solvent compositions include $(CH_3CH_2O(CO)OCH_2)_2$:EC in the indicated ratio.
The three-component $(CH_3CH_2O(CO)OCH_2)_2$:solvent composition includes $(CH_3CH_2O(CO)OCH_2)_2$:ethylene carbonate:triglyme in the indicated ratio.

In Table III, the abbreviations are as follows: EC, ethylene carbonate; and TrG, triglyme ($C_8H_{18}O_4$). It may be seen that electrolyte films may be formed from a combination of a liquid electrolyte plasticizer, a suitable amount of PVdF, a high dielectric constant solvent, a lithium salt, and, optionally, a glyme. As in the preceding Example, it may be seen that the ambient temperature conductivity may be varied as desired by choosing different relative quantities of plasticizer, solvent or glyme in the conductive composition.

We claim:

1. An ion conductive composition having enhanced ambient temperature conductivity comprising:

(a) a liquid electrolyte plasticizer having the structure

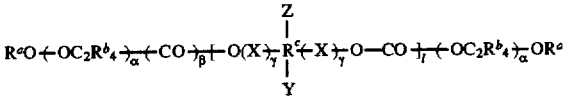

wherein $R^a$ is independently selected from the group consisting of alkyl, —(CO)$OR^d$, —$(C_pH_{2p})_x$—$(OC_2R^b_4)_\alpha$—$OR^d$,

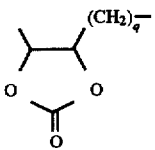

and

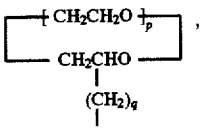

and $R^b$ is independently selected from the group consisting of H, alkyl, aryl, alkenyl, fluoro, and fluorinated lower alkyl, $R^c$ is alkylene or —$(C_pH_{2p})_p$—$(OC_2R^b_4)_\alpha$—m $R^d$ is H or alkyl, X is lower alkylene, Y is selected from the group consisting of H, aryl and alkyl, Z is selected from the group consisting of H and $CH_2O(CO)OR^a$, $\alpha, \gamma, l, \rho$ and $\tau$ are integers in the range of 0 to 10 inclusive, $\beta$ is 0, 1 or 2, p is an integer in the ravage of 1 to 5 inclusive, and q is an integer in the range of 0 to 6 inclusive; and (b) an ion conductive material selected from the group a salt of the formula C-A, wherein C is a cation and A is an anion and a single-ion conducting polymer electrolyte.

2. The ion conductive composition of claim 1, wherein the ion conductive material is a salt of the formula C-A.

3. The ion conductive composition of claim 2, wherein C is selected from the group consisting of groups IA, IB, IIA, and IIB, elements.

4. The ion conductive composition of claim 3, wherein C is lithium.

5. The ion conductive composition of claim 4, wherein A is $PF_6$.

6. An ion conductive film having enhanced ambient temperature ion conductivity and mechanical strength, comprising the ion conductive composition of claim 5 and an amount of a strengthening material effective to enhance the mechanical strength of the film.

7. A solid state battery comprising a positive electrode, a negative electrode and the ion conductive composition of claim 5.

8. The ion conductive composition of claim 4, wherein A is $N(CF_3SO_2)_2$.

9. An ion conductive film having enhanced ambient temperature ion conductivity and mechanical strength, comprising the ion conductive composition of claim 8 and an amount of a strengthening material effective to enhance the mechanical strength of the film.

10. A solid state battery comprising a positive electrode, a negative electrode and the ion conductive composition of claim 8.

11. The ion conductive composition of claim 3, wherein C is sodium.

12. The ion conductive composition of claim 2, wherein A is selected from the group consisting of Cl, $CF_3SO_2$, $ClO_4$, $BF_4$, Br, I, SCN, $AsF_6$, $N(CF_3SO_2)_2$, $PF_6$, $SbF_6$, and $O(CO)R^i$, wherein $R^i$ is H, alkyl, aryl, alkenyl, halo, haloalkyl.

13. The ion conductive composition of claim 12, wherein A is $PF_6$.

14. The ion conductive composition of claim 12, wherein A is $N(CF_3SO_2)_2$.

15. An ion conductive film having enhanced ambient temperature ion conductivity and mechanical strength, comprising the ion conductive composition of claim 2 and an amount of a strengthening material effective to enhance the mechanical strength of the film.

16. A solid state battery comprising a positive electrode, a negative electrode and the ion conductive composition of claim 2.

17. The ion conductive composition of claim 1, wherein the ion conductive material is a single-ion conducting polymer electrolyte.

18. The ion conductive composition of claim 17, wherein the single-ion conducting polymer electrolyte has the structure

wherein:

$R^1$ and $R^2$ are individually selected from the group consisting of moieties having the structure

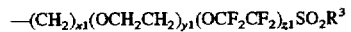

in which x1 and z1 may be the same or different and are integers in the range of 1 to 100 inclusive, y1 is an integer in the range of 0 to 100 inclusive, and $R^3$ is —OM, —$N(M)SO_2CF_3$ or —$C(M)(SO_2CF_3)_2$ and M is an alkali metal, or wherein one of $R^1$ and $R^2$ has the structure

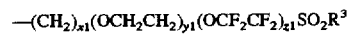

and the other is selected from the group consisting of hydrogen, lower alkyl, fluorinated lower alkyl, lower alkenyl, fluorinated lower alkenyl, aryl and aralkylene; and n is an integer indicating the number of mer units in the polymer.

19. An ion conductive film having enhanced ambient temperature ion conductivity and mechanical strength comprising the ion conductive composition of claim 18 and an amount of a strengthening material effective to enhance the mechanical strength of the film.

20. A solid state battery comprising a positive electrode, a negative electrode and the ion conductive composition of claim 18.

21. An ion conductive film having enhanced ambient temperature ion conductivity and mechanical strength, comprising the ion conductive composition of claim 17 and an amount of a strengthening material effective to enhance the mechanical strength of the film.

22. A solid state battery comprising a positive electrode, a negative electrode and the ion conductive composition of claim 17.

23. An ion conductive film having enhanced ambient temperature ion conductivity and mechanical strength, comprising the ion conductive composition of claim 1 and an amount of a stregthening material effective to enhance the mechanical strength of the film.

24. A solid state battery comprising a positive electrode, a negative electrode and the ion conductive composition of claim 1.

* * * * *